(12) United States Patent
Orr (10) Patent No.: US 8,660,971 B2
(45) Date of Patent: Feb. 25, 2014

(54) SYSTEM AND METHOD FOR DETECTING RESPIRATORY INSUFFICIENCY IN THE BREATHING OF A SUBJECT

(75) Inventor: Joseph Allen Orr, Park City, UT (US)

(73) Assignee: Koninklijke Philips N.V., Eindhoven (NL)

( * ) Notice: Subject to any disclaimer, the term of this patent is extended or adjusted under 35 U.S.C. 154(b) by 251 days.

(21) Appl. No.: 13/121,002

(22) PCT Filed: Oct. 9, 2009

(86) PCT No.: PCT/IB2009/054456
§ 371 (c)(1),
(2), (4) Date: Mar. 25, 2011

(87) PCT Pub. No.: WO2010/044040
PCT Pub. Date: Apr. 22, 2010

(65) Prior Publication Data
US 2011/0178968 A1     Jul. 21, 2011

Related U.S. Application Data

(60) Provisional application No. 61/105,446, filed on Oct. 15, 2008.

(51) Int. Cl.
*G06E 1/00* (2006.01)
*G06E 3/00* (2006.01)
*G06F 15/18* (2006.01)
*G06G 7/00* (2006.01)

(52) U.S. Cl.
USPC ............................................................ 706/20

(58) Field of Classification Search
None
See application file for complete search history.

(56) References Cited

U.S. PATENT DOCUMENTS

| 2004/0003813 | A1* | 1/2004 | Banner et al. | 128/204.21 |
| 2005/0256420 | A1* | 11/2005 | Norman et al. | 600/533 |
| 2007/0293779 | A1* | 12/2007 | Bardy | 600/529 |
| 2008/0009762 | A1 | 1/2008 | Hampton | |
| 2008/0216834 | A1* | 9/2008 | Easley et al. | 128/204.23 |

OTHER PUBLICATIONS

Patel, Mahish M. et al "Neural Network Analysis of the Volumetric Capnogram to Detect Pulmonary Embolish" Chest, vol. 116, No. 5, Nov. 1999, pp. 1325-1332.

\* cited by examiner

*Primary Examiner* — Kakali Chaki
*Assistant Examiner* — Mario Riojas Ramirez (57) ABSTRACT

Respiratory insufficiency is detected by classifying preliminary breaths identified through a capnogram as being valid or artifact. Individual breaths are classified as being valid or artifact by determining values of a plurality of breathing parameters for a given breath, inferring a value for a key parameter from the determined values for the plurality of breathing parameters, and comparing the inferred value for the key parameter to a predetermined threshold.

17 Claims, 6 Drawing Sheets

SYSTEM AND METHOD FOR DETECTING RESPIRATORY INSUFFICIENCY IN THE BREATHING OF A SUBJECT

BACKGROUND OF THE INVENTION

1. Field of the Invention

The invention pertains to the detection of respiratory insufficiency in the breathing of a subject, and the generation of an artificial neural network for use in such detection.

2. Description of the Related Art

The technique of monitoring capnogram samples of gas at or near the airway of a non-intubated subject to detect respiratory insufficiency in the breathing of the subject is known. Generally, this technique relies on the fluctuation of $CO_2$ present in the airway of the subject as the subject inhales (reducing $CO_2$ levels) and exhales (increasing $CO_2$ levels). However, this technique has a drawback in that there are various circumstances in which the subject is not breathing, or not breathing sufficiently, that may not be detected by conventional systems implementing this technique.

For example, the subject may make attempts at breathing without moving sufficient volume of gas into and out of the lungs. These small, un-productive breaths can be caused by over-sedation or by airway obstruction, among other things. Unfortunately, simple capnometry may not be capable of discerning these small, inadequate breaths from safe tidal breathing. As another example, cardiogenic oscillations are a phenomenon in which the beating of the heart causes very small movements of gas into and out of the lungs. While these movements of gas may be detected by conventional systems as sufficient respiration, the amount of gas moved will not be enough to sustain the subject.

SUMMARY OF THE INVENTION

One aspect of the invention relates to a system configured to detect respiratory insufficiency. In one embodiment, the system comprises one or more processors configured to obtain information related to the breathing of a subject, and to execute one or more modules. In one embodiment, the one or more modules comprise a parameter module, a key parameter module, and a classification module. The parameter module is configured to determine parameters of the breathing of the subject based on the information obtained by the processor. The key parameter module is configured to infer a value for a key parameter of the breathing of the subject from the parameters determined by the parameter module, the key parameter being a parameter that is not directly derivable from the information obtained by the processor. The classification module is configured to detect respiratory insufficiency in the breathing of the subject by comparing the inferred value of the key parameter to a predetermined threshold.

Another aspect of the invention relates to a method of detecting respiratory insufficiency. In one embodiment of the invention, the method comprises obtaining information related to the breathing of a subject; determining parameters of the breathing of the subject based on the obtained information; inferring a value for a key parameter of the breathing of the subject from the determined parameters, the key parameter being a parameter that is not directly derivable from the obtained information related to the breathing of the subject; and detecting respiratory insufficiency in the breathing of the subject by comparing the inferred value of the key parameter to a predetermined threshold.

Yet another aspect of the invention relates to a system configured to detect respiratory insufficiency. In one embodiment, the system comprises means for obtaining information related to the breathing of a subject; means for determining parameters of the breathing of the subject based on the obtained information; means for inferring a value for a key parameter of the breathing of the subject from the determined parameters, the key parameter being a parameter that is not directly derivable from the obtained information related to the breathing of the subject; and means for detecting respiratory insufficiency in the breathing of the subject by comparing the inferred value of the key parameter to a predetermined threshold.

Still another aspect of the invention relates to a system configured to generate an artificial neural network that models a relationship between a predetermined set of breathing parameters and a key parameter. In one embodiment, the system comprises an input interface and one or more processors. The input interface is configured to obtain sets of information that correspond to the breathing of individual ones of a plurality of test subjects, the information being related to a set of breathing parameters including a key parameter, the key parameter being an indicator of breathing deficiency. The one or more processors execute one or more modules. In one embodiment, the one or more modules comprises a parameter module and a modeling module. The parameter module is configured to determine values for the set of breathing parameters for breaths of individual ones of the test subjects from the obtained sets of information. The modeling module is configured to generate an artificial neural network that models a relationship between the value of the key parameter and the values of the other ones of the set of breathing parameters, the modeling module generating the artificial neural network from the values determined by the parameter module.

Still another aspect of the invention relates to A method of generating an artificial neural network that models a relationship between a predetermined set of breathing parameters and a key parameter. In one embodiment, the method comprises obtaining sets of information that correspond to the breathing of individual ones of a plurality of test subjects, the information being related to a set of breathing parameters including a key parameter, the key parameter being an indicator of breathing deficiency; determining values for the set of breathing parameters for breaths of individual ones of the test subjects from the obtained sets of information; and generating an artificial neural network that models a relationship between the value of the key parameter and the values of the other ones of the set of breathing parameters, the artificial neural network being generated from the values for the set of breathing parameters for breaths of individual ones of the test subjects.

Still another aspect of the invention relates to a system configured to generate an artificial neural network that models a relationship between a predetermined set of breathing parameters and a key parameter. In one embodiment, the system comprises means for obtaining sets of information that correspond to the breathing of individual ones of a plurality of test subjects, the information being related to a set of breathing parameters including a key parameter, the key parameter being an indicator of breathing deficiency; means for determining values for the set of breathing parameters for breaths of individual ones of the test subjects from the obtained sets of information; and means for generating an artificial neural network that models a relationship between the value of the key parameter and the values of the other ones of the set of breathing parameters, the artificial neural network being generated from the values for the set of breathing parameters for breaths of individual ones of the test subjects.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
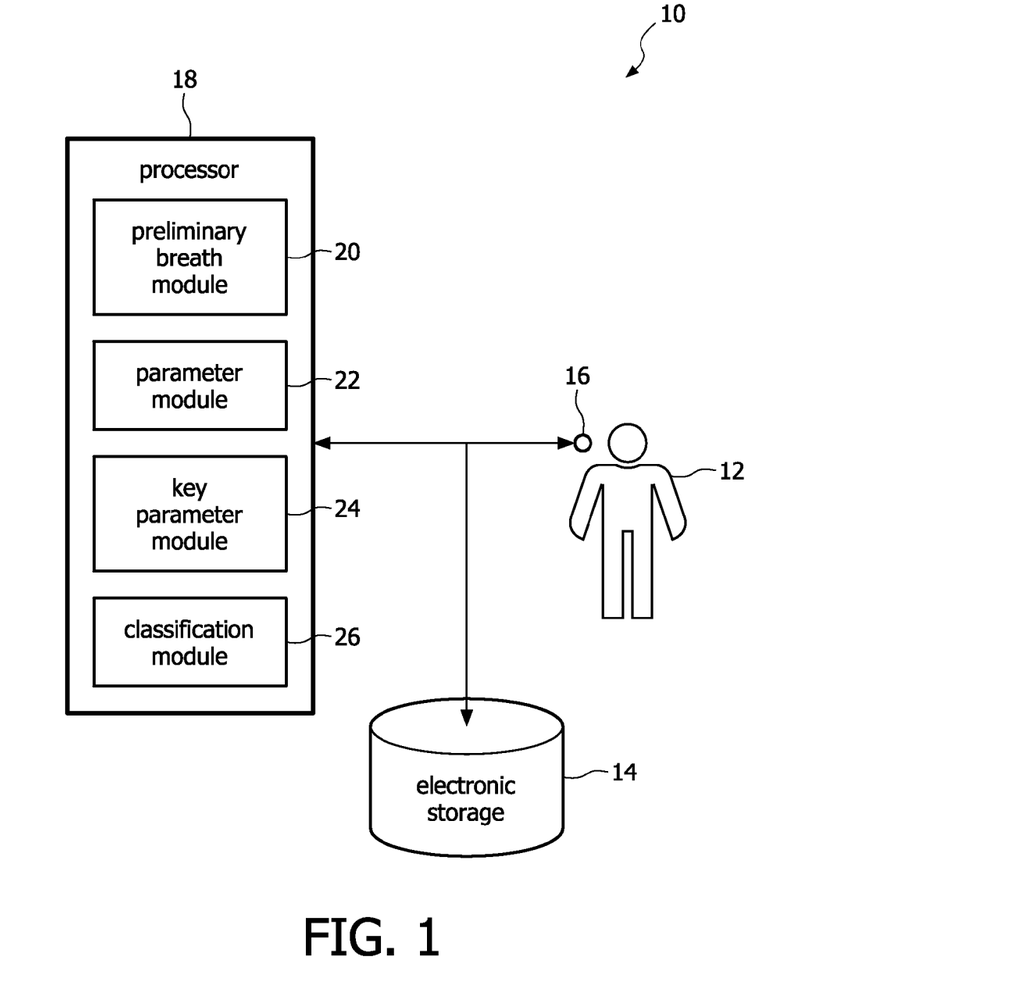
FIG. 1 illustrates a system configured to detect respiratory insufficiency, in accordance with one or more embodiments of the invention.

FIG. 1 illustrates a system 10 configured to detect respiratory insufficiency in the breathing of a subject 12. In particular, system 10 implements signals generated by capnometric sensors and/or other sensors to preliminarily identify breaths of subject 12, and to determine whether the preliminarily identified breaths are valid, productive breaths, or artifact, deficient breaths. As such, system 10 may be deployed to non-invasively monitor the sufficiency of respiration of subject 12, e.g., in instances in which subject 12 is not intubated. In one embodiment, system 10 includes an electronic storage 14, one or more sensors 16, and a processor 18.

In one embodiment, electronic storage 14 comprises electronic storage media that electronically stores information. The electronically storage media of electronic storage 14 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 14 may store software algorithms, information determined by processor 18, output signals (or information derived from output signals) generated by sensor 16, and/or other information that enables system 10 to function properly. Electronic storage 14 may be a separate component within system 10, or electronic storage 14 may be provided integrally with one or more other components of system 10 (e.g., processor 18).

In one embodiment, sensor 16 is configured to generate output signals that convey information related to one or more parameters of gas at or near the airway of subject 12. The discussion of sensor 16 as a single component is not intended to be limiting, as sensor 16 may include a plurality of sensors. In one embodiment, sensor 16 includes a capnometric sensor generating output signals that convey information related to the concentration of $CO_2$ at or near the airway of subject 12. This is not intended to be limiting. In some embodiments, sensor 16 includes other types of sensors, such as oxygen, flow, pressure, temperature, and/or humidity sensors, along with the capnometric sensor, or includes other types of sensors instead of the capnometric sensor. The output signals generated by sensor 16 are communicated to one or both of processor 18 and/or electronic storage 14.

In order to generate output signals that convey information related to one or more parameters of gas at or near the airway of subject 12, sensor 16 is in communication with this gas. For example, in one embodiment, sensor 16 is provided with a respiration circuit (not shown and also referred to as a "patient circuit") that guides gas to and/or receives gas from the airway of subject 12. The respiration circuit may include one or more conduits capable of conveying gas to and/or from subject 12 and an interface appliance configured to communicate gas between the airway of subject 12 and the one or more conduits. By way of non-limiting example, the interface appliance may include one or more of a nasal cannula, a nasal/oral combination cannula, a gas delivery mask, and/or other interface appliances.

Processor 18 is configured to provide information processing capabilities in system 10. As such, processor 18 may include one or more of a digital processor, an analog processor, a digital circuit designed to process information, an analog circuit designed to process information, a state machine, and/or other mechanisms for electronically processing information. Although processor 18 is shown in FIG. 1 as a single entity, this is for illustrative purposes only. In some implementations, processor 18 may include a plurality of processing units. These processing units may be physically located within the same device, or processor 18 may represent processing functionality provided by a plurality of devices operating in coordination.

As is shown in FIG. 1, in one embodiment, processor 18 includes a preliminary breath module 20, a parameter module 22, a key parameter module 24, a classification module 26, and/or other modules. Modules 20, 22, 24, and/or 26 may be implemented in software; hardware; firmware; some combination of software, hardware, and/or firmware; and/or otherwise implemented. It should be appreciated that although modules 20, 22, 24, and 26 are illustrated in FIG. 1 as being co-located within a single processing unit, in implementations in which processor 18 includes multiple processing units, modules 20, 22, 24, and/or 26 may be located remotely from the other modules. Further, the description of the functionality provided by the different modules 20, 22, 24, and/or 26 described below is for illustrative purposes, and is not intended to be limiting, as any of modules 20, 22, 24, and/or 26 may provide more or less functionality than is described. For example, one or more of modules 20, 22, 24, and/or 26 may be eliminated, and some or all of its functionality may be provided by other ones of modules 20, 22, 24, and/or 26. As another example, processor 18 may include one or more additional modules that may perform some or all of the functionality attributed below to one of modules 20, 22, 24, and/or 26.

Preliminary breath module 20 is configured to perform an initial analysis of the output signals generated by sensor 16 to preliminarily identify individual breaths of subject 12. Due to the preliminary nature of this analysis, breaths identified by preliminary breath module 20 are referred to herein as "preliminary breaths." This does not refer to the quality of the breaths taken by subject 12, but only the level of analysis provided by preliminary breath module 20 in identifying respiration.

In one embodiment, sensor 16 generates output signals the convey information related to the concentration of $CO_2$ in gas at or near the airway of subject 12. In this embodiment, preliminary breath module 20 identifies a breath based on a deviation of the concentration of $CO_2$ above and below a predetermined threshold. Because $CO_2$ increases during exhalation and decreases during inspiration, the deviation of the concentration of $CO_2$ above and below the predetermined threshold is preliminarily identified by preliminary breath module 20 as a preliminary breath, e.g., an inhalation and exhalation. In order to refine somewhat the identification of preliminary breaths by preliminary breath module 20, preliminary breath module 20 may apply a hysteresis (e.g., corresponding to 5 mm Hg) as the concentration of $CO_2$ passes back and forth across the threshold.

Parameter module 22 is configured to determine a plurality of parameters of the breathing of subject 12 from the output signals generated by sensor 16. The plurality of parameters are determined on a per preliminary breath basis. As non-limiting examples, the plurality of parameters determined by parameter module 22 may include one or more of a time ratio between the time of inspiration and the time of expiration, a fraction of inspiration time during which the level of $CO_2$ is some predetermined amount less than the maximum $CO_2$ level during a breath (e.g., less than 10% of the maximum $CO_2$ level), a difference between the maximum partial pressure of $CO_2$ observed during a breath and the partial pressure of $CO_2$ observed a predetermined period of time (e.g., 100 ms, 200 ms, 300 ms, 400 ms, 500 ms, etc.) prior to the point in time at which the maximum was observed, a fraction of expiration time during a breath when a capnogram is within 10% of the maximum $CO_2$ detected during the breath, a standard deviation of capnogram samples taken during inspiration, a mean of capnogram samples taken during inspiration, and/or other parameters.

In one embodiment, parameters determined by parameter module 22 are normalized. By way of non-limiting example, a value determined by parameter module 22 for a given parameter may be subtracted from a first predetermined value for the given parameter, e.g., a mean for the given parameter determined in previous testing. Normalization may include dividing the value determined by parameter module 22 for the given parameter, or the difference between the determined value and the first predetermined value, by a second predetermined value for the given parameter, e.g., a standard deviation from the mean determined in previous testing.

In one embodiment, the plurality of parameters determined by parameter module 22 includes values determined by aggregating samples of the level of $CO_2$ during a given breath. The values may be determined as means of $CO_2$ levels, median $CO_2$ levels, cumulative $CO_2$ levels and/or other aggregations of measure $CO_2$ levels determined from a plurality of samples. For example, one parameter may be determined from the first 10 (or some other number) of samples of the level of $CO_2$ during a given breath, another parameter may be determined from the next 10 (or some other number) of samples of the level of $CO_2$ during the given breath, and so on. In this embodiment, a short breath may not provide enough sample points to provide data from which each of the values can be determined, e.g., 300 samples are used, but one breath happens to only last for 200 samples. In such instances, samples not provided in the information received from sensor 16 may be automatically assigned a preset value, e.g., zero (0), and the parameters determined from the assigned values.

Key parameter module 24 is configured to infer a value for a key parameter of the breathing of the subject from the parameters determined by parameter module 22. Because the parameters determined by parameter module 22 are determined on a per preliminary breath basis, the key parameter is inferred by key parameter module 24 on a per preliminary breath basis. The key parameter is a parameter of the breathing of subject 12 that is not directly quantifiable from the output signals generated by sensor 16. The key parameter is a parameter of the breathing of subject 12, which, if measured directly, would provide a more accurate classification of preliminary breaths as artifact or valid than the parameters quantifiable directly from the output signals generated by sensor 16. For example, the key parameter may include one or more of expired volume, peak respiratory flow, maximum airway pressure, chest wall movement, and/or other key parameters. In one embodiment, key parameter module 24 infers the value for the key parameter from an artificial neural network that uses as inputs the parameters determined by parameter module 22, and outputs a value for the key parameter. By way of non-limiting example, the neural network may implement 10 parameters determined by parameter module 22 as inputs and/or may have 20 hidden layer nodes that lead to a single output, the key parameter.

Classification module 26 is configured to analyze the values for the key parameter inferred by key parameter module 24 to detect respiratory insufficiency in the breathing of subject 12. In one embodiment, classification module 26 detects respiratory insufficiency in the breathing of subject 12 by comparing a value of the key parameter for a given preliminary breath with a predetermined threshold. The predetermined threshold may be configured by a user, e.g., a caregiver, subject 12, etc. Based on this comparison, classification module 26 determines if the given preliminary breath is an artifact breath, or a valid breath. Determinations of a certain number of consecutive artifact breaths, and/or a determination of a number of artifact breaths in a certain amount of time and/or a certain amount of preliminary breaths may indicate overall respiratory insufficiency in the breathing of subject 12. In one embodiment for example, classification module 26 determines a respiratory rate to convey the sufficiency of respiration by subject 12. If a valid breath is detected by classification module 26, then classification module 26 updates a calculation of respiratory rate to reflect the newly detected valid breath. If an artifact breath is detected, then classification does not update the calculation of respiratory rate until the next valid breath is detected.

By way of non-limiting example, in one embodiment, the key parameter is expired volume, and the predetermined threshold is a minimum expired breath volume. Key parameter module 24 infers a value for expired volume of a given preliminary breath from the parameters determined for the given preliminary breath by parameter module 22. Classification module 26 compares the inferred value for expired volume for the given preliminary breath with the threshold volume. If the inferred value is greater than the threshold volume, then the given preliminary breath is classified as a valid breath. If the inferred value is less than the threshold volume, then the preliminary breath is classified as an artifact breath. Based on the classification of the given preliminary breath and other preliminary breaths in this manner, classification module 26 is able to detect respiratory insufficiency in the breathing of subject 12.

Figure 2:
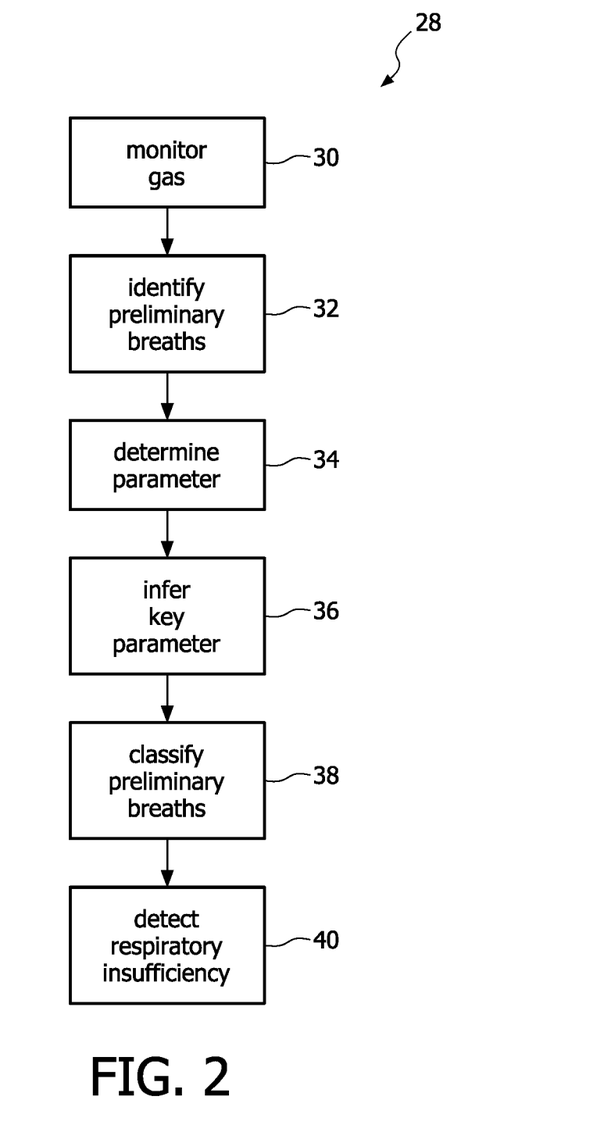
FIG. 2 illustrates a method of detecting respiratory insufficiency, according to one or more embodiments of the invention.

FIG. 2 illustrates a method 28 of detecting respiratory insufficiency in the respiration of a subject. The operations of method 28 presented below are intended to be illustrative. In some embodiments, method 28 may be accomplished with one or more additional operations not described, and/or without one or more of the operations discussed. Additionally, the order in which the operations of method 28 are illustrated in FIG. 2 and described below is not intended to be limiting. In some embodiments, method 28 is implemented by a system that is the same as or similar to system 10 (shown in FIG. 1 and described above). It should be appreciated that this does not limit the scope of this disclosure, as method 28 may be implemented in a variety of other system configurations.

At an operation 30, gas at or near the airway of the subject is monitored. In one embodiment, operation 30 is performed by one or more sensors that are the same as or similar to sensor 16 (shown in FIG. 1 and described above), and are in communication with gas at or near the airway of the subject.

At an operation 32, individual breaths of the subject are preliminarily identified as preliminary breaths. The identification of preliminary breaths at operation 32 is based on information generated by the monitoring of gas at operation 30. In one embodiment, operation 32 is performed by a preliminary breath module that is the same as or similar to preliminary breath module 20 (shown in FIG. 1 and described above).

At an operation 34, parameters of the breathing of the subject are determined. The parameters are determined on a per preliminary breath basis. The parameters are determined based on information generated by the monitoring of gas at operation 30. The parameters may include one or more of a time ratio between the time of inspiration and the time of expiration, a fraction of inspiration time during which the level of $CO_2$ is some predetermined amount less than the maximum $CO_2$ level during a breath (e.g., less than 10% of the maximum $CO_2$ level), a difference between the maximum partial pressure of $CO_2$ observed during a breath and the partial pressure of $CO_2$ observed a predetermined period of time (e.g., 100 ms, 200 ms, 300 ms, 400 ms, 500 ms, etc.) prior to the point in time at which the maximum was observed, a fraction of expiration time during a breath when a capnogram is within 10% of the maximum $CO_2$ detected during the breath, a standard deviation of capnogram samples taken during inspiration, a mean of capnogram samples taken during inspiration, and/or other parameters. In one embodiment, parameters determined at operation 34 are normalized. By way of non-limiting example, a value determined at operation 34 for a given parameter may be subtracted from a first predetermined value for the given parameter, e.g., a mean for the given parameter determined in previous testing. Normalization may include dividing the value determined at operation 34, or the difference between the determined value and the first predetermined value, by a second predetermined value for the given parameter (e.g., a standard deviation from the mean determined in previous testing). In one embodiment, operation 34 is performed by a parameter module that is the same as or similar to parameter module 22 (shown in FIG. 1 and described above).

At an operation 36, a key parameter of the breathing of the subject is inferred. The key parameter is inferred on a per preliminary breath basis. The key parameter is not directly quantifiable from the information generated at operation 30, but is inferred from the parameters determined at operation 34. The key parameter is a parameter of the breathing of the subject, which, if measured directly, would provide a more accurate classification of preliminary breaths as artifact or valid than the parameters derivable directly from the information generated at operation 30. For example, the key parameter may include one or more of expired volume, peak respiratory flow, maximum airway pressure, chest wall movement, and/or other key parameters. In one embodiment, the value for the key parameter is inferred at operation 36 from an artificial neural network that uses as inputs the parameters determined at operation 34, and outputs a value for the key parameter. In one embodiment, operation 36 is performed by a key parameter module that is the same as or similar to key parameter module 24 (shown in FIG. 1 and described above).

At an operation 38, preliminary breaths are classified as artifact breaths or valid breaths. A given preliminary breath is classified based on the corresponding value determined for the key parameter at operation 36. For example, the value determined for the key parameter at operation 36 for a given preliminary breath may be compared with a predetermined threshold, and the given preliminary breath may then be classified as artifact or valid based on this comparison. In one embodiment, operation 38 is performed by a classification module that is the same as or similar to classification module 26 (shown in FIG. 1 and described above).

At an operation 40, overall respiratory insufficiency is determined from the classification of preliminary breaths at operation 38. This determination may based on a predetermined number of consecutive artifact breaths, a proportion of artifact breaths to total preliminary breaths over a certain number of preliminary breast, and/or otherwise based on the classification of preliminary breaths at operation 38. In one embodiment for example, operation 40 determines a respiratory rate to convey the sufficiency of respiration by the subject. If a valid breath is detected at operation 38, then operation 40 includes updating a calculation of respiratory rate to reflect the newly detected valid breath. If an artifact breath is detected, then operation 40 does not update the calculation of respiratory rate until the next valid breath is detected. In one embodiment, operation 40 is performed by the classification module.

Figure 3:
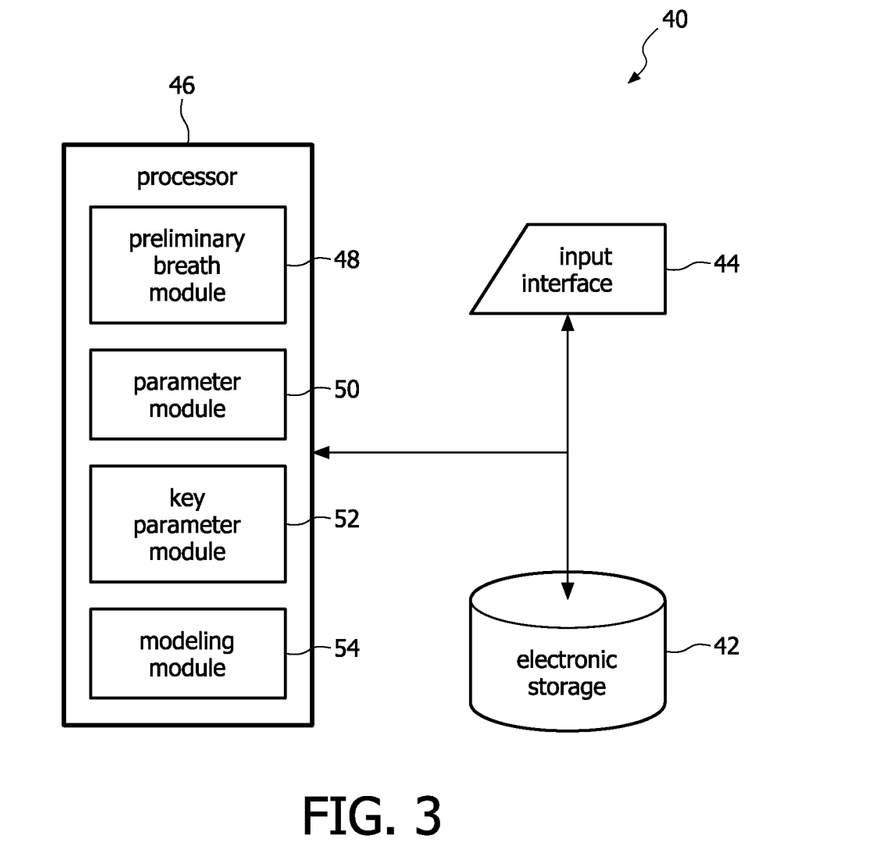
FIG. 3 illustrates a system configured to generate an artificial neural network that models a relationship between a plurality of breathing parameters and a key parameter, in accordance with one or more embodiments of the invention.

FIG. 3 illustrates a system 40 configured to generate an artificial neural network that models a relationship between a predetermined set of breathing parameters and a key parameter. The key parameter is a breathing parameter that provides a relatively accurate indication as to whether a given perceived breath is an effective, valid breath, or a deficient, artifact breath. The artificial neural network generated by system 40 may be implemented to infer a value of the key parameter from measured values for the other breathing parameters (e.g., in system 10 shown in FIG. 1 and described above). In one embodiment, system 40 includes electronic storage 42, input interface 44, and a processor 46.

In one embodiment, electronic storage 42 comprises electronic storage media that electronically stores information. The electronically storage media of electronic storage 42 may include one or both of system storage that is provided integrally (i.e., substantially non-removable) with system 40 and/or removable storage that is removably connectable to system 40 via, for example, a port (e.g., a USB port, a firewire port, etc.) or a drive (e.g., a disk drive, etc.). Electronic storage 42 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 42 may store software algorithms, information determined by processor 46, information obtained by input interface 44, and/or other information that enables system 40 to function properly. Electronic storage 42 may be a separate component within system 40, or electronic storage 42 may be provided integrally with one or more other components of system 40 (e.g., processor 46).

Input interface 44 is configured to provide an interface between system 40 and one or more information sources through which information is received by system 40. This enables data, results, and/or instructions and any other communicable items, collectively referred to as "information," to be communicated to one or both of processor 46 and/or electronic storage 42. Examples of interface devices suitable for inclusion in input interface 44 include a keypad, buttons, switches, a keyboard, knobs, levers, a display screen, a touch screen, speakers, a microphone, an indicator light, an audible alarm, and/or a printer.

It is to be understood that other communication techniques, either hard-wired or wireless, are also contemplated by the present invention as input interface 44. For example, the present invention contemplates that input interface may be integrated with a removable storage interface provided by electronic storage 42. In this example, information may be loaded into system 40 from removable storage (e.g., a smart card, a flash drive, a removable disk, etc.) that enables the user(s) to customize the implementation of system 40. Other exemplary input devices and techniques adapted for use with system 40 as user interface 40 include, but are not limited to, an RS-232 port, an RF link, an IR link, modem (telephone, cable or other). In short, any technique for communicating information with system 40 is contemplated by the present invention as input interface 44.

During operation, input interface 44 is configured to obtain sets of information that correspond to the breathing of individual ones of a plurality of test subjects. The sets of information form a training data set that is used to derive the artificial neural network generated by system 40. The information includes output signals (or information derived from output signals) of one or more sensors (not shown) in communication with gas at the airways of the test subjects during respiration by the test subjects. For example, the one or more sensors may include sensors that are the same as or similar to sensor 16 shown in FIG. 1 and described above. During the testing of the test subjects, the test subjects may be administered one or more substances that induce sedation to a level that impacts the respiration of the subjects. In particular, the level of sedation will ensure that, for at least some of the test subjects, the sufficiency of respiration is depressed below normal levels. For example, the test subject may be administered controlled infusions of propofol and remifentanil. In one embodiment, input interface 44 collects data from each test subject for between 6 and 8 hours.

Referring to FIG. 3, in one embodiment, the information obtained by input interface 44 includes output signals from which a plurality of breathing parameters can be derived. For example, the output signals may include output signals generated by capnometric sensors in communication with gas at or near the airways of the test subjects. These output signals convey information related to the concentration of $CO_2$ in the gas at or near the airways of the test subjects. The information obtained by input interface 44 also includes output signals from which values for a key parameter can be directly derived. The key parameter is a parameter of the breathing of the test subjects that is not directly quantifiable from the output signals from which the other breathing parameters are determined. Instead, the output signals from which the key parameter is directly derived are generated by a separate set of one or more sensors, not likely utilized in some therapeutic situations, or that would be difficult or unwieldy in some therapeutic situations. The key parameter provides for a more accurate classification of preliminary breaths as artifact or valid than the other breathing parameters for which information is obtained by input interface 44. For example, the key parameter may include one or more of expired volume, peak respiratory flow, maximum airway pressure, chest wall movement, and/or other key parameters.

Processor 46 is configured to provide information processing capabilities in system 40. As such, processor 46 may include one or more of a digital processor, an analog processor, a digital circuit designed to process information, an analog circuit designed to process information, a state machine, and/or other mechanisms for electronically processing information. Although processor 46 is shown in FIG. 3 as a single entity, this is for illustrative purposes only. In some implementations, processor 46 may include a plurality of processing units. These processing units may be physically located within the same device, or processor 46 may represent processing functionality provided by a plurality of devices operating in coordination.

As is shown in FIG. 3, in one embodiment, processor 46 includes a preliminary breath module 48, a parameter module 50, a key parameter module 52, a modeling module 54, and/or other modules. Modules 48, 50, 52, and/or 54 may be implemented in software; hardware; firmware; some combination of software, hardware, and/or firmware; and/or otherwise implemented. It should be appreciated that although modules 48, 50, 52, and 54 are illustrated in FIG. 3 as being co-located within a single processing unit, in implementations in which processor 46 includes multiple processing units, modules 48, 50, 52, and/or 54 may be located remotely from the other modules. Further, the description of the functionality provided by the different modules 48, 50, 52, and/or 54 described below is for illustrative purposes, and is not intended to be limiting, as any of modules 48, 50, 52, and/or 54 may provide more or less functionality than is described. For example, one or more of modules 48, 50, 52, and/or 54 may be eliminated, and some or all of its functionality may be provided by other ones of modules 48, 50, 52, and/or 54. As another example, processor 18 may include one or more additional modules that may perform some or all of the functionality attributed below to one of modules 48, 50, 52, and/or 54.

Preliminary breath module 48 analyzes the information related to the breathing parameters, other than the key parameter, obtained by input interface 44 and identifies individual preliminary breaths in the breathing of the individual test subjects. As was mentioned above, in one embodiment, the information obtained by input interface 44 includes output signals that convey information related to the concentration of $CO_2$ in gas at or near the airways of the test subjects during breathing. In this embodiment, preliminary breath module 48 identifies a preliminary breath in the breathing of an individual test subject based on a deviation of the concentration of $CO_2$ above and below a predetermined threshold in substantially the same manner as preliminary breath module 20 (shown in FIG. 1 and described above).

Parameter module 50 is configured to determine the breathing parameters of the breathing of the test subjects, other than the key parameter, from the information obtained by input interface 44. The breathing parameters are determined on a per preliminary breath basis. Thus, for each preliminary breath identified in the breathing of each of the test subject, parameter module 50 determines corresponding values for each of the breathing parameters (other than the key parameter) from the information obtained by input interface 44. As non-limiting examples, the breathing parameters determined by parameter module 50 may include one or more of a time ratio between the time of inspiration and the time of expiration, a fraction of inspiration time during which the level of $CO_2$ is some predetermined amount less than the maximum $CO_2$ level during a breath (e.g., less than 10% of the maximum $CO_2$ level), a difference between the maximum partial pressure of $CO_2$ observed during a breath and the partial pressure of $CO_2$ observed a predetermined period of time (e.g., 100 ms, 200 ms, 300 ms, 400 ms, 500 ms, etc.) prior to the point in time at which the maximum was observed, a fraction of expiration time during a breath when a capnogram is within 10% of the maximum $CO_2$ detected during the breath, a standard deviation of capnogram samples taken during inspiration, a mean of capnogram samples taken during inspiration, and/or other parameters.

In one exemplary embodiment, upon completion of testing of a plurality of test subjects, values that enable normalization of future determinations of the parameters are determined by parameter module 50. By way of non-limiting example, a first predetermined value may be determined by parameter module 50 to be subtracted from future determinations of a given parameter (e.g., a mean for the given parameter determined in previous testing) and/or a second predetermined value may be determined by which future determinations of the given parameter (or differences between the future determinations and the first predetermined value) are to be divided (e.g., a standard deviation from the mean determined in previous testing).

In one embodiment, the breathing parameters determined by parameter module 22 include values determined by aggregating samples of the level of $CO_2$ during a given breath. The values may be determined as means of $CO_2$ levels, median $CO_2$ levels, cumulative $CO_2$ levels and/or other aggregations of measure $CO_2$ levels determined from a plurality of samples. For example, one breathing parameter may be determined from the first 10 (or some other number) of samples of the level of $CO_2$ during a given breath, another breathing parameter may be determined from the next 10 (or some other number) of samples of the level of $CO_2$ during the given breath, and so on. In this embodiment, a short breath may not provide enough sample points to provide data from which each of the values can be determined (e.g., 300 samples are used, but one breath happens to only last for 200 samples). In such instances, samples not provided in the information received from sensor 16 may be automatically assigned a preset value (e.g., 0), and the breathing parameters determined from the assigned values.

Key parameter module 52 is configured to determine the key parameter from the information obtained by input interface 44. The key parameter is derived directly from the information obtained by input interface 44 on a per preliminary breath basis. Key parameter module 52 is able derive values for the key parameter directly from the information obtained by input interface 44 because, as was mentioned above, the information obtained by input interface 44 includes output signals generated by sensors not typically in use during certain therapeutic situations. The result of the determinations performed by key parameter module 52 is a directly measured set of values for the key parameter that correspond to the individual preliminary breaths identified by preliminary breath module 48 in the breathing of the test subjects.

Modeling module 54 is configured to generate an artificial neural network that models a relationship between the value of the key parameter and the values of the other breathing parameters. As used herein, the term "artificial neural network" refers to a mathematical and/or computational model based on biological neural networks. An artificial neural network may include an interconnected group of artificial neurons, and may process information using a connectionist approach to computation. Various search algorithms and network architectures have been devised to best model the relationship between a given set of input data and the corresponding desired output within the paradigm of artificial neural networks. As such, a detailed description of the techniques used by modeling module 54 to generate the artificial neural network from the parameters derived by processor 46 is not undertaken herein. The artificial neural network generated by modeling module 54 models the relationship between the value of key parameter and the values of the other breathing parameters in that the artificial neural network uses as inputs the breathing parameters for a given breath, and outputs a value for the key parameter for the given breath.

Figure 4:
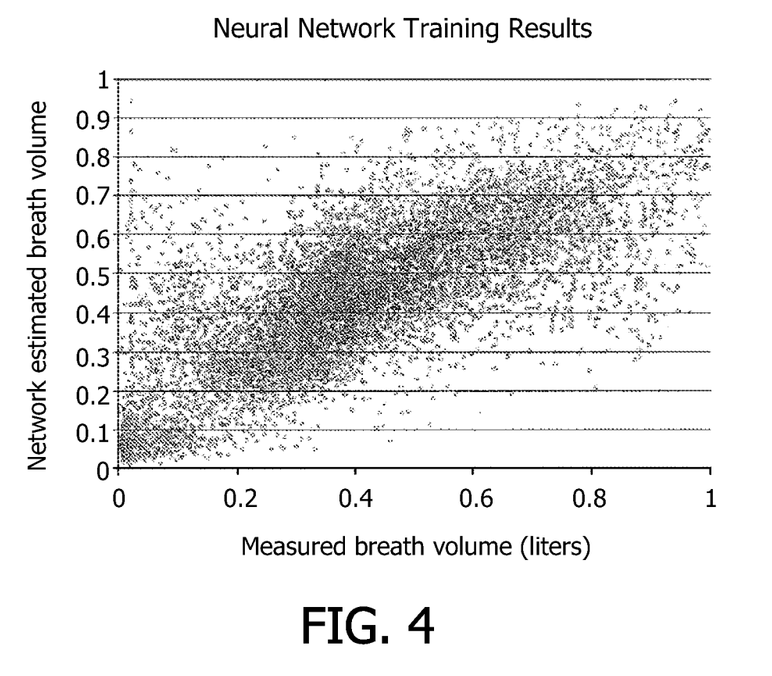
FIG. 4 illustrates a plot of measured values for a key parameter of individual breaths versus values inferred according to an artificial neural network, according one or more exemplary embodiments of the invention

In one exemplary embodiment, the artificial neural network generated by modeling module 54 was tested to ensure its effectiveness. For example, in one embodiment, only a portion of the data collected from the test subjects is implemented by processor 46 to generate the artificial neural network in the manner described above. The remainder of the data is then implemented to test the generated artificial neural network. This enables inferred values for the key parameter to be compared directly with measured values for the key parameter (which may not be possible in clinical usage). For example, FIG. 4 illustrates a plot of data points where the key parameter is breath volume, the x-axis is the measured values for individual breaths, and the y-axis are valued inferred from an artificial neural network generated by system 40.

Figure 5:
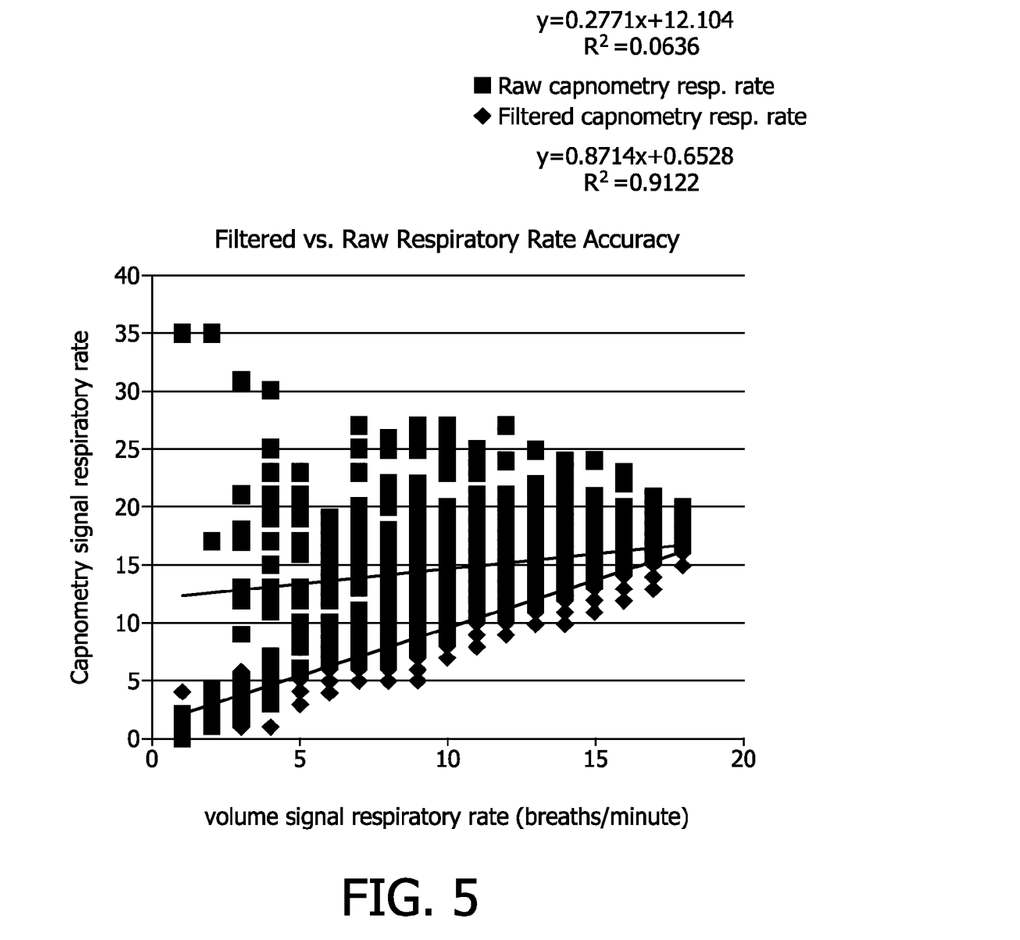
FIG. 5 illustrates a plot of measured respiratory rates versus respiratory rates inferred from breaths identified as valid or artifact by an artificial neural network, in accordance with one or more exemplary embodiments of the invention.

Similarly, the implementation of some of the collected test data to test the artificial neural network enables a respiratory rate determined from direct measurement of the key parameter to be compared with the respiratory rate determined implementing the artificial neural network to infer the respiratory rate. By way of example, FIG. 5 illustrates a plot respiratory rate determinations for individual test subjects where the x-axis represents the respiratory rates of test subject determined from direct measurements of the key parameter (breath volume), and the y-axis represents the respiratory rates of the same test subjects as determined by (i) conventional methods (the square shaped points), and (ii) according to the inference of the key parameter according to the artificial neural network (the diamond shaped points). As can be seen in FIG. 5, the rate determined based on valid breaths identified by the artificial neural network provides an enhanced accuracy over determinations in which capnometry measurements alone are used to identify breaths.

Figure 6:
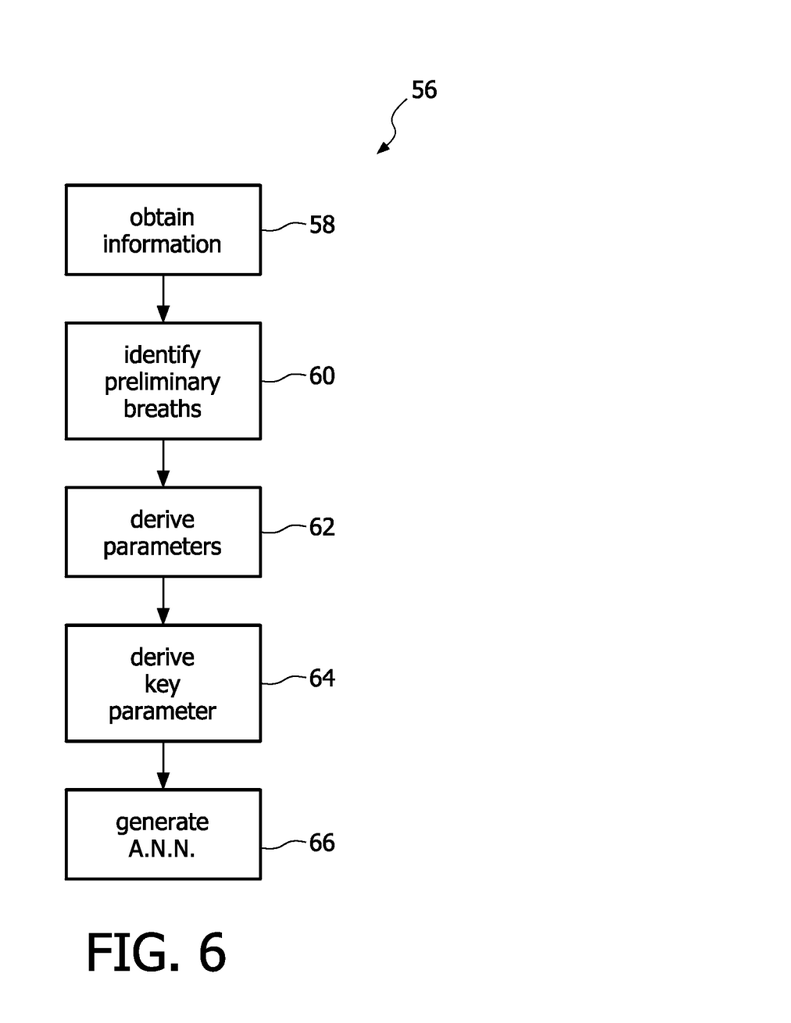
FIG. 6 illustrates a method of generating an artificial neural network that models a relationship between a plurality of breathing parameters and a key parameter, according to one or more embodiments of the invention.

FIG. 6 illustrates a method 56 of generating an artificial neural network that models a relationship between a predetermined set of breathing parameters and a key parameter. The operations of method 56 presented below are intended to be illustrative. In some embodiments, method 56 may be accomplished with one or more additional operations not described, and/or without one or more of the operations discussed. Additionally, the order in which the operations of method 56 are illustrated in FIG. 4 and described below is not intended to be limiting. In some embodiments, method 56 is implemented by a system that is the same as or similar to system 40 (shown in FIG. 3 and described above). It should be appreciated that this does not limit the scope of this disclosure, as method 56 may be implemented in a variety of other system configurations.

At an operation 58, sets of information that correspond to the breathing of individual ones of a plurality of test subjects are obtained. The sets of information form a training data set that is used to derive the artificial neural network generated by method 56. The information includes output signals (or information derived from output signals) of one or more sensors (not shown) in communication with gas at the airways of the test subjects during respiration by the test subjects. The information obtained at operation 58 includes information from which a plurality of breathing parameters can be derived. For example, the information may include capnogram samples of gas at or near the airways of the test subjects. The information obtained at operation 58 also includes information from which a key parameter can be directly derived. The key parameter is a parameter of the breathing of the test subjects that is not directly quantifiable from the information used to determine the other breathing parameters, e.g., the capnogram samples. Instead, the information from which the key parameter is directly derived corresponds to output signals generated by a separate set of one or more sensors not likely utilized in some therapeutic situations. The key parameter provides for a more accurate classification of preliminary breaths as artifact or valid than the other breathing parameters for which information is obtained at operation 58. For example, the key parameter may include one or more of expired volume, peak respiratory flow, maximum airway pressure, chest wall movement, and/or other key parameters. In one embodiment, operation 58 is performed by in input interface that is the same as or similar to input interface 44 (shown in FIG. 3 and described above).

At an operation 60, information obtained at operation 58 related to the breathing parameters, other than the key parameter, is analyzed to preliminarily identify individual preliminary breaths in the breathing of the individual test subjects. In one embodiment, operation 60 is performed by a preliminary breath module that is the same as or similar to preliminary breath module 48 (shown in FIG. 3 and described above).

At an operation 62, the breathing parameters of the breathing of the test subjects, other than the key parameter, are determined from the information obtained at operation 58. The breathing parameters are determined on a per preliminary breath basis. Thus, for each preliminary breath identified in the breathing of each of the test subject at operation 60, corresponding values for each of the breathing parameters (other than the key parameter) are determined at operation 62. As non-limiting examples, the breathing parameters determined at operation 62 may include one or more of a time ratio between the time of inspiration and the time of expiration, a fraction of inspiration time during which the level of $CO_2$ is some predetermined amount less than the maximum $CO_2$ level during a breath (e.g., less than 10% of the maximum $CO_2$ level), a difference between the maximum partial pressure of $CO_2$ observed during a breath and the partial pressure of $CO_2$ observed a predetermined period of time (e.g., 100 ms, 200 ms, 300 ms, 400 ms, 500 ms, etc.) prior to the point in time at which the maximum was observed, a fraction of expiration time during a breath when a capnogram is within 10% of the maximum $CO_2$ detected during the breath, a standard deviation of capnogram samples taken during inspiration, a mean of capnogram samples taken during inspiration, and/or other parameters (e.g., the parameters discussed above with respect to parameter module 50). In one embodiment, operation 62 is performed by a parameter module that is the same as or similar to parameter module 50 (shown in FIG. 3 and described above).

At an operation 64, the key parameter is determined directly from the information obtained at operation 58. The key parameter is derived on a per preliminary breath basis. Values for the key parameter are derived directly from the information obtained at operation 58 because, as was mentioned above, the information obtained at operation 58 includes information corresponding to output signals generated by sensors not typically in use during certain therapeutic situations. The result of the determinations performed at operation 64 is a directly measured set of values for the key parameter that correspond to the individual preliminary breaths in the breathing of the test subjects identified at operation 60.

At an operation 66, an artificial neural network modeling the relationship between the breathing parameters determined at operation 62 and the key parameter is generated. The artificial neural network generated at operation 66 uses as inputs the breathing parameters for a given breath, and outputs a value for the key parameter for the given breath. In one embodiment, operation 66 is performed by a modeling module that is the same as or similar to modeling module 54 (shown in FIG. 3 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to detect respiratory insufficiency, the system comprising:
   (a) one or more processors configured to obtain information related to the breathing of a subject, and to execute one or more modules, the one or more modules comprising:
   (1) a parameter module configured to determine parameters of the breathing of the subject based on the information obtained by the processor, wherein the parameters are determined on a per preliminary breath basis, wherein the preliminary breath basis refers to individual breaths and not to a quality of the breaths, but only a level of analysis in identifying respiration,
   (2) a key parameter module configured to infer a value for a key parameter of the breathing of the subject on a per preliminary breath basis from the parameters determined by the parameter module, wherein the key parameter is a parameter not directly derivable from the information obtained by the processor, further wherein the key parameter module includes an artificial neural network that models a relationship between a predetermined set of breathing parameters and the key parameter, wherein responsive to inputs of the breathing parameters for a given preliminary breath, the artificial neural network outputs the value for the key parameter for the given preliminary breath, and
   (3) a classification module configured to detect respiratory insufficiency in the breathing of the subject by (i) comparing the inferred value of the key parameter for a given preliminary breath to a predetermined threshold, (ii)

classifying, in response to the comparison, individual preliminary breaths as being (ii)(a) valid, productive breaths or (ii)(b) artifact, deficient breaths, respectively, and (iii) responsive to the classification of individual preliminary breaths, determining an overall respiratory insufficiency, wherein determining the overall respiratory insufficiency includes determining a respiratory rate to convey sufficiency of respiration of the subject, wherein (iii)(a) responsive to detection of a valid, productive breath, updating a calculation of respiratory rate to reflect the detected valid, productive breath, and (iii)(b) responsive to detection of an artifact, deficient breath, not updating the calculation of respiratory rate until a next valid, productive breath is detected, wherein the parameters determined by the parameter module include values determined by aggregating predetermined sets of samples of $CO_2$ levels during a given preliminary breath, wherein (i) a first parameter is determined from a first set that comprises a first number of samples of the level of $CO_2$ during the given preliminary breath, (ii) another parameter is determined from a next set that comprises a next number of samples of the level of $CO_2$ during the same given preliminary breath, and (iii) responsive to the given preliminary breath being a short breath not providing enough sample points to provide data from which each of the parameter values can be determined, the parameter module (iii)(a) automatically assigns preset values to those sample points that are not provided because of the short breath and (iii)(b) determines a corresponding parameter with use of the assigned values.

2. The system of claim 1, wherein the classification module detects respiratory insufficiency in the breathing of the subject if the inferred value of the key parameter crosses the threshold.

3. The system of claim 1, wherein the key parameter includes one or more of expired volume, peak respiratory flow, maximum airway pressure, or chest wall movement.

4. The system of claim 1, wherein the predetermined threshold is configurable by a user.

5. The system of claim 1, wherein the parameters determined by the parameter module include one or more of a time ratio between the time of inspiration and the time of expiration, a fraction of inspiration time during which the level of $CO_2$ is some predetermined amount less than the maximum $CO_2$ level during a breath, a difference between the maximum partial pressure of $CO_2$ observed during a breath and the partial pressure of $CO_2$ observed a predetermined period of time prior to the point in time at which the maximum was observed, a fraction of expiration time during a breath when a capnogram is within 10% of the maximum $CO_2$ detected during the breath, a standard deviation of capnogram samples taken during inspiration, or a mean of capnogram samples taken during inspiration.

6. The system of claim 1, wherein the information obtained by the processor includes output signals generated by one or more sensors in communication with gas provided to and/or received from the airway of the subject.

7. A method of detecting respiratory insufficiency, the method comprising:
obtaining information related to the breathing of a subject;
determining parameters of the breathing of the subject based on the obtained information, wherein the parameters are determined on a per preliminary breath basis, wherein the preliminary breath basis refers to individual breaths and not to a quality of the breaths, but only a level of analysis in identifying respiration;
inferring a value for a key parameter of the breathing of the subject on a per preliminary breath basis from the determined parameters, wherein the key parameter is a parameter not directly derivable from the obtained information related to the breathing of the subject, further wherein inferring the key parameter includes using an artificial neural network that models a relationship between a predetermined set of breathing parameters and the key parameter, wherein responsive to inputs of the breathing parameters for a given preliminary breath, the artificial neural network outputs the value for the key parameter for the given preliminary breath; and
detecting respiratory insufficiency in the breathing of the subject by (i) comparing the inferred value of the key parameter for a given preliminary breath to a predetermined threshold, (ii) classifying, in response to the comparison, individual preliminary breaths as being (ii)(a) valid, productive breaths or (ii)(b) artifact, deficient breaths, respectively, and (iii) responsive to the classification of individual preliminary breaths, determining an overall respiratory insufficiency, wherein determining the overall respiratory insufficiency includes determining a respiratory rate to convey sufficiency of respiration of the subject, wherein (iii)(a) responsive to detection of a valid, productive breath, updating a calculation of respiratory rate to reflect the detected valid, productive breath, and (iii)(b) responsive to detection of an artifact, deficient breath, not updating the calculation of respiratory rate until a next valid, productive breath is detected, wherein the parameters determined from the obtained information related to the breathing of the subject include values determined by aggregating predetermined sets of samples of $CO_2$ levels during a given preliminary breath wherein (i) a first parameter is determined from a first set that comprises a first number of samples of the level of $CO_2$ during the given preliminary breath (ii) another parameter is determined from a next set that comprises a next number of samples of the level of $CO_2$ during the same given preliminary breath, and (iii) responsive to the given preliminary breath being a short breath not providing enough sample points to provide data from which each of the parameter values can be determined, (iii)(a) automatically assigning preset values to those sample points that are not provided because of the short breath and (iii)(b) determining a corresponding parameter with use of the assigned values.

8. The method of claim 7, wherein respiratory insufficiency in the breathing of the subject is detected if the inferred value of the key parameter crosses the threshold.

9. The method of claim 7, wherein the key parameter includes one or more of expired volume, peak respiratory flow, maximum airway pressure, or chest wall movement.

10. The method of claim 7, wherein the predetermined threshold is configurable by a user.

11. The method of claim 7, wherein the parameters determined from the obtained information related to the breathing of the subject include one or more of a time ratio between the time of inspiration and the time of expiration, a fraction of inspiration time during which the level of $CO_2$ is some predetermined amount less than the maximum $CO_2$ level during a breath, a difference between the maximum partial pressure of $CO_2$ observed during a breath and the partial pressure of $CO_2$ observed a predetermined period of time prior to the point in time at which the maximum was observed, a fraction of expiration time during a breath when a capnogram is within 10% of the maximum $CO_2$ detected during the breath, a standard deviation of capnogram samples taken during inspiration, or a mean of capnogram samples taken during inspiration.

12. The method of claim 7, wherein the obtained information related to the breathing of the subject includes output signals generated by one or more sensors in communication with gas provided to and/or received from the airway of the subject.

13. A system configured to detect respiratory insufficiency, the system comprising:
    means for obtaining information related to the breathing of a subject;
    means for determining parameters of the breathing of the subject based on the obtained information, wherein the parameters are determined on a per preliminary breath basis, wherein the preliminary breath basis refers to individual breaths and not to a quality of the breaths, but only a level of analysis in identifying respiration;
    means for inferring a value for a key parameter of the breathing of the subject on a per preliminary breath basis from the determined parameters, wherein the key parameter is a parameter not directly derivable from the obtained information related to the breathing of the subject, further wherein inferring the key parameter includes using an artificial neural network that models a relationship between a predetermined set of breathing parameters and the key parameter, wherein responsive to inputs of the breathing parameters for a given preliminary breath, the artificial neural network outputs the value for the key parameter for the given preliminary breath; and
    means for detecting respiratory insufficiency in the breathing of the subject by (i) comparing the inferred value of the key parameter for a given preliminary breath to a predetermined threshold, (ii) classifying, in response to the comparison, individual preliminary breaths as being (ii)(a) valid, productive breaths or (ii)(b) artifact, deficient breaths, respectively, and (iii) responsive to the classification of individual preliminary breaths, determining an overall respiratory insufficiency, wherein determining the overall respiratory insufficiency includes determining a respiratory rate to convey sufficiency of respiration of the subject, wherein (iii)(a) responsive to detection of a valid, productive breath, updating a calculation of respiratory rate to reflect the detected valid, productive breath, and (iii)(b) responsive to detection of an artifact, deficient breath, not updating the calculation of respiratory rate until a next valid, productive breath is detected, wherein the parameters determined from the obtained information related to the breathing of the subject include values determined by aggregating predetermined sets of samples of $CO_2$ levels during a given preliminary breath wherein (i) a first parameter is determined from a first set that comprises a first number of samples of the level of $CO_2$ during the given preliminary breath, (ii) another parameter is determined from a next set that comprises a next number of samples of the level of $CO_2$ during the same given preliminary breath, and (iii) responsive to the given preliminary breath being a short breath not providing enough sample points to provide data from which each of the parameter values can be determined, (iii)(a) automatically assigning preset values to those sample points that are not provided because of the short breath and (iii)(b) determining a corresponding parameter with use of the assigned values.

14. The system of claim 13, wherein respiratory insufficiency in the breathing of the subject is detected if the inferred value of the key parameter crosses the threshold.

15. The system of claim 13, wherein the key parameter includes one or more of expired volume peak respiratory flow, maximum airway pressure, or chest wall movement.

16. The system of claim 13, wherein the parameters determined obtained information related to the breathing of the subject include one or more of a time ratio between the time of inspiration and the time of expiration, a fraction of inspiration time during which the level of $CO_2$ is some predetermined amount less than the maximum $CO_2$ level during a breath, a difference between the maximum partial pressure of $CO_2$ observed during a breath and the partial pressure of $CO_2$ observed a predetermined period of time prior to the point in time at which the maximum was observed, a fraction of expiration time during a breath when a capnogram is within 10% of the maximum $CO_2$ detected during the breath, a standard deviation of capnogram samples taken during inspiration, or a mean of capnogram samples taken during inspiration.

17. The system of claim 13, wherein the obtained information related to the breathing of the subject includes output signals generated by one or more sensors in communication with gas provided to and/or received from the airway of the subject.

* * * * *